United States Patent
Zinn

(10) Patent No.: US 11,547,843 B2
(45) Date of Patent: *Jan. 10, 2023

(54) VENOUS ACCESS PORT ASSEMBLY WITH X-RAY DISCERNABLE INDICIA

(71) Applicant: Innovative Medical Devices, LLC, Westport, CT (US)

(72) Inventor: Kenneth M. Zinn, Westport, CT (US)

(73) Assignee: Innovative Medical Devices, LLC, Westport, CT (US)

( * ) Notice: Subject to any disclaimer, the term of this patent is extended or adjusted under 35 U.S.C. 154(b) by 351 days.

This patent is subject to a terminal disclaimer.

(21) Appl. No.: 16/851,459

(22) Filed: Apr. 17, 2020

(65) Prior Publication Data

US 2020/0261709 A1    Aug. 20, 2020

Related U.S. Application Data

(63) Continuation of application No. 15/441,762, filed on Feb. 24, 2017, now Pat. No. 10,639,465, which is a
(Continued)

(51) Int. Cl.
*A61M 39/02* (2006.01)
*A61M 39/00* (2006.01)

(52) U.S. Cl.
CPC . *A61M 39/0208* (2013.01); *A61M 2039/0045* (2013.01); *A61M 2039/0226* (2013.01); *A61M 2039/0238* (2013.01); *A61M 2205/32* (2013.01)

(58) Field of Classification Search
CPC ...... A61M 39/0208; A61M 2039/0045; A61M 2039/0226; A61M 2039/0238; A61M 2039/0258; A61M 2205/32
See application file for complete search history.

(56) References Cited

U.S. PATENT DOCUMENTS

| | | |
|---|---|---|
| 574,387 A | 1/1897 | Buckler |
| 611,357 A | 9/1898 | Dembinski |

(Continued)

FOREIGN PATENT DOCUMENTS

| | | |
|---|---|---|
| DE | 8437873 U1 | 3/1986 |
| DE | 3447202 A1 | 7/1986 |

(Continued)

OTHER PUBLICATIONS

Guidance for Industry and FDA Staff, Use of Symbols on Labels and in Labeling of In Vitro Diagnostic Devices Intended for Professional Use, Nov. 30, 2004, 12 pages.
(Continued)

*Primary Examiner* — Nathan R Price
*Assistant Examiner* — Justin L Zamory

(57) ABSTRACT

A venous access port assembly having a housing base with a discharge stem, a cap, and an interior reservoir. The port assembly is provided with X-ray discernable indicia to identify an attribute of the assembly after its implantation and clearly appear on an X-ray of the patient in a manner informing the radiologist or technologist and the medical practitioner of that particular attribute. The indicia are cuts in a reservoir lining of radiopaque material such as metal where the cuts having narrow slot width are in the form of one or more sets of alphabetical letters such as "CT" in the lining's side wall or bottom wall.

10 Claims, 3 Drawing Sheets

Related U.S. Application Data continuation of application No. 12/175,270, filed on Jul. 17, 2008, now Pat. No. 9,610,432.

(60) Provisional application No. 60/961,160, filed on Jul. 19, 2007.

(56) References Cited

U.S. PATENT DOCUMENTS

| | | |
|---|---|---|
| 966,696 A | 8/1910 | Merrill |
| 1,713,267 A | 5/1929 | Crowley |
| 2,029,553 A | 2/1936 | Bartschi et al. |
| 2,433,480 A | 12/1947 | Rendich |
| 2,891,689 A | 6/1959 | Gould |
| D198,453 S | 6/1964 | Weichselbaum |
| 3,293,663 A | 12/1966 | Cronin |
| 3,341,417 A | 9/1967 | Sinaiko |
| 3,518,428 A | 6/1970 | Ring |
| 3,529,633 A | 9/1970 | Vaillancourt |
| 3,643,358 A | 2/1972 | Morderosian |
| 3,829,904 A | 8/1974 | Ling et al. |
| 3,831,583 A | 8/1974 | Edmunds et al. |
| 3,840,009 A | 10/1974 | Michaels et al. |
| 3,891,997 A | 7/1975 | Herbert |
| 3,915,162 A | 10/1975 | Miller |
| 3,919,724 A | 11/1975 | Sanders et al. |
| 3,922,726 A | 12/1975 | Trentani et al. |
| 3,951,147 A | 4/1976 | Tucker et al. |
| 4,027,391 A | 6/1977 | Samis |
| 4,035,653 A | 7/1977 | Karasko |
| 4,121,108 A | 10/1978 | Manor |
| 4,123,806 A | 11/1978 | Amstutz et al. |
| 4,168,586 A | 9/1979 | Samis |
| 4,181,132 A | 1/1980 | Parks |
| 4,190,040 A | 2/1980 | Schulte |
| 4,190,057 A | 2/1980 | Downie et al. |
| 4,194,122 A | 3/1980 | Mitchell et al. |
| 4,202,349 A | 5/1980 | Jones |
| 4,222,374 A | 9/1980 | Sampson et al. |
| 4,233,964 A | 11/1980 | Jefferts et al. |
| 4,274,006 A | 6/1981 | Caine |
| 4,349,498 A | 9/1982 | Ellis et al. |
| 4,361,153 A | 11/1982 | Slocum et al. |
| 4,405,305 A | 9/1983 | Stephen et al. |
| 4,406,567 A | 9/1983 | Samis |
| 4,425,119 A | 1/1984 | Berglund |
| 4,445,896 A | 5/1984 | Gianturco |
| 4,450,592 A | 5/1984 | Niederer et al. |
| 4,450,985 A | 5/1984 | Beard |
| 4,456,011 A | 6/1984 | Warnecke |
| 4,469,483 A | 9/1984 | Becker et al. |
| 4,494,545 A | 1/1985 | Slocum et al. |
| 4,506,676 A | 3/1985 | Duska |
| 4,529,635 A | 7/1985 | Sheldon |
| 4,543,088 A | 9/1985 | Bootman et al. |
| 4,549,879 A | 10/1985 | Groshong et al. |
| 4,559,046 A | 12/1985 | Groshong et al. |
| 4,560,375 A | 12/1985 | Schulte et al. |
| 4,571,749 A | 2/1986 | Fischell |
| 4,576,595 A | 3/1986 | Aas et al. |
| 4,587,954 A | 5/1986 | Haber |
| 4,612,877 A | 9/1986 | Hayes et al. |
| 4,626,244 A | 12/1986 | Reinicke |
| 4,627,844 A | 12/1986 | Schmitt |
| 4,634,427 A | 1/1987 | Hannula et al. |
| 4,636,194 A | 1/1987 | Schulte et al. |
| 4,636,213 A | 1/1987 | Pakiam |
| 4,653,508 A | 3/1987 | Cosman |
| 4,655,765 A | 4/1987 | Swift |
| 4,657,024 A | 4/1987 | Coneys |
| 4,662,652 A | 5/1987 | Hargis |
| 4,668,221 A | 5/1987 | Luther |
| 4,671,796 A | 6/1987 | Groshong et al. |
| 4,673,394 A | 6/1987 | Fenton, Jr. et al. |
| 4,684,365 A | 8/1987 | Reinicke |
| 4,685,447 A | 8/1987 | Iversen et al. |
| 4,685,905 A | 8/1987 | Jeanneret |
| 4,692,146 A | 9/1987 | Hilger |
| 4,695,273 A | 9/1987 | Brown |
| 4,697,595 A | 10/1987 | Breyer et al. |
| 4,701,166 A | 10/1987 | Groshong et al. |
| 4,704,103 A | 11/1987 | Stoeber et al. |
| 4,710,174 A | 12/1987 | Moden et al. |
| 4,718,894 A | 1/1988 | Lazorthes |
| 4,728,894 A | 3/1988 | Yoda et al. |
| 4,743,231 A | 5/1988 | Kay et al. |
| 4,753,640 A | 6/1988 | Nichols et al. |
| 4,755,173 A | 7/1988 | Konopka et al. |
| 4,760,837 A | 8/1988 | Petit |
| 4,762,517 A | 8/1988 | McIntyre et al. |
| 4,767,410 A | 8/1988 | Moden et al. |
| 4,772,270 A | 9/1988 | Wiita et al. |
| 4,772,276 A | 9/1988 | Wiita et al. |
| 4,773,552 A | 9/1988 | Boege et al. |
| 4,778,452 A | 10/1988 | Moden et al. |
| 4,781,680 A | 11/1988 | Redmond et al. |
| 4,781,685 A | 11/1988 | Lehmann et al. |
| 4,781,695 A | 11/1988 | Dalton |
| 4,802,885 A | 2/1989 | Weeks et al. |
| 4,804,054 A | 2/1989 | Howson et al. |
| 4,820,273 A | 4/1989 | Reinicke |
| 4,822,341 A | 4/1989 | Colone |
| 4,840,615 A | 6/1989 | Hancock et al. |
| 4,848,346 A | 7/1989 | Crawford |
| 4,857,053 A | 8/1989 | Dalton |
| 4,861,341 A | 8/1989 | Woodburn |
| 4,863,470 A | 9/1989 | Carter |
| 4,886,501 A | 12/1989 | Johnston et al. |
| 4,892,518 A | 1/1990 | Cupp et al. |
| 4,904,241 A * | 2/1990 | Bark ............... A61M 39/0208 604/117 |
| 4,905,709 A | 3/1990 | Bieganski et al. |
| 4,909,250 A | 3/1990 | Smith |
| 4,915,690 A | 4/1990 | Cone et al. |
| 4,928,298 A | 5/1990 | Tanaka |
| 4,929,236 A | 5/1990 | Sampson |
| 4,955,861 A | 9/1990 | Enegren et al. |
| 4,963,133 A | 10/1990 | Whipple |
| 4,966,583 A | 10/1990 | Debbas |
| 4,973,319 A | 11/1990 | Melsky |
| 4,983,162 A | 1/1991 | Metais et al. |
| 5,002,735 A | 3/1991 | Mberhasky et al. |
| 5,009,644 A | 4/1991 | Mcdonald |
| 5,013,298 A | 5/1991 | Moden et al. |
| 5,041,098 A | 8/1991 | Loiterman et al. |
| 5,044,955 A | 9/1991 | Jagmin |
| 5,045,060 A | 9/1991 | Melsky et al. |
| 5,045,064 A | 9/1991 | Idriss |
| 5,084,015 A | 1/1992 | Moriuchi |
| 5,085,216 A | 2/1992 | Henley et al. |
| 5,090,066 A | 2/1992 | Schoepe et al. |
| 5,092,849 A | 3/1992 | Sampson |
| 5,108,317 A | 4/1992 | Beinhaur et al. |
| 5,108,377 A | 4/1992 | Cone et al. |
| 5,112,301 A | 5/1992 | Fenton et al. |
| 5,112,303 A | 5/1992 | Pudenz et al. |
| 5,129,891 A | 7/1992 | Young |
| 5,137,529 A | 8/1992 | Watson et al. |
| 5,147,483 A | 9/1992 | Melsky et al. |
| 5,152,753 A | 10/1992 | Laguette et al. |
| 5,156,600 A | 10/1992 | Young |
| 5,158,547 A | 10/1992 | Doan et al. |
| 5,167,629 A | 12/1992 | Vertenstein et al. |
| 5,167,633 A | 12/1992 | Mann et al. |
| 5,167,638 A | 12/1992 | Felix et al. |
| 5,171,228 A | 12/1992 | Mcdonald |
| 5,176,653 A | 1/1993 | Metals |
| 5,176,662 A | 1/1993 | Bartholomew et al. |
| 5,178,612 A | 1/1993 | Fenton, Jr. |
| 5,185,003 A | 2/1993 | Brethauer |
| 5,189,690 A | 2/1993 | Samuel |
| 5,193,106 A | 3/1993 | Desena |
| 5,195,122 A | 3/1993 | Fabian |
| 5,195,123 A | 3/1993 | Clement |
| 5,201,715 A | 4/1993 | Masters |

(56) References Cited

U.S. PATENT DOCUMENTS

| | | |
|---|---|---|
| 5,203,771 A | 4/1993 | Melker |
| 5,203,777 A | 4/1993 | Lee |
| 5,215,537 A | 6/1993 | Lynn et al. |
| 5,222,499 A | 6/1993 | Allen et al. |
| D337,637 S | 7/1993 | Tucker |
| 5,224,938 A | 7/1993 | Fenton, Jr. |
| 5,263,930 A | 11/1993 | Ensminger |
| 5,281,205 A | 1/1994 | Mcpherson |
| 5,290,263 A | 3/1994 | Wigness et al. |
| 5,295,658 A | 3/1994 | Atkinson et al. |
| 5,299,253 A | 3/1994 | Wessels |
| 5,309,863 A | 5/1994 | Leeb, Jr. |
| 5,312,337 A | 5/1994 | Flaherty et al. |
| 5,318,545 A | 6/1994 | Tucker |
| 5,320,100 A | 6/1994 | Herweck et al. |
| 5,322,511 A | 6/1994 | Armbruster et al. |
| 5,328,480 A | 7/1994 | Melker et al. |
| 5,332,398 A | 7/1994 | Miller et al. |
| 5,334,153 A | 8/1994 | Mcintyre et al. |
| 5,336,194 A | 8/1994 | Polaschegg et al. |
| 5,338,398 A | 8/1994 | Szwejkowski et al. |
| 5,350,360 A | 9/1994 | Ensminger et al. |
| 5,352,204 A | 10/1994 | Ensminger |
| 5,360,407 A | 11/1994 | Leonard et al. |
| 5,383,233 A | 1/1995 | Russell |
| 5,383,858 A | 1/1995 | Reilly et al. |
| D355,240 S | 2/1995 | Gladfelter et al. |
| 5,387,192 A | 2/1995 | Glantz et al. |
| 5,394,457 A | 2/1995 | Leibinger et al. |
| 5,395,324 A | 3/1995 | Hinrichs et al. |
| 5,397,329 A | 3/1995 | Allen |
| 5,399,168 A | 3/1995 | Wadsworth et al. |
| 5,405,402 A | 4/1995 | Dye et al. |
| 5,417,565 A | 5/1995 | Long |
| 5,417,656 A | 5/1995 | Ensminger et al. |
| 5,421,814 A | 6/1995 | Geary |
| 5,423,334 A | 6/1995 | Jordan |
| 5,425,762 A | 6/1995 | Muller |
| 5,433,480 A | 7/1995 | Gresham et al. |
| 5,456,698 A | 10/1995 | Byland et al. |
| 5,476,460 A | 12/1995 | Montalvo |
| 5,476,588 A | 12/1995 | Nagaoka |
| 5,484,402 A | 1/1996 | Saravia et al. |
| 5,503,630 A | 4/1996 | Ensminger et al. |
| 5,507,813 A | 4/1996 | Dowd et al. |
| 5,509,805 A | 4/1996 | Jagmin |
| 5,513,637 A | 5/1996 | Twiss et al. |
| 5,514,103 A | 5/1996 | Srisathapat et al. |
| 5,520,632 A | 5/1996 | Leveen et al. |
| 5,527,277 A | 6/1996 | Ensminger et al. |
| 5,527,307 A | 6/1996 | Srisathapat et al. |
| 5,531,684 A | 7/1996 | Ensminger et al. |
| 5,556,381 A | 9/1996 | Ensminger et al. |
| 5,558,641 A | 9/1996 | Glantz et al. |
| 5,562,617 A | 10/1996 | Finch et al. |
| 5,562,618 A | 10/1996 | Cai et al. |
| 5,575,770 A | 11/1996 | Melsky et al. |
| 5,607,393 A | 3/1997 | Ensminger et al. |
| 5,607,407 A | 3/1997 | Tolkoff et al. |
| 5,613,945 A | 3/1997 | Cai et al. |
| 5,620,419 A | 4/1997 | Lui et al. |
| 5,632,729 A | 5/1997 | Cai et al. |
| 5,637,102 A | 6/1997 | Tolkoff et al. |
| 5,638,832 A | 6/1997 | Singer et al. |
| 5,647,855 A | 7/1997 | Trooskin |
| 5,662,600 A | 9/1997 | Watson et al. |
| 5,662,612 A | 9/1997 | Niehoff |
| 5,676,146 A | 10/1997 | Scarborough |
| 5,695,490 A | 12/1997 | Flaherty et al. |
| 5,702,128 A | 12/1997 | Maxim et al. |
| 5,702,363 A | 12/1997 | Flaherty |
| 5,704,915 A | 1/1998 | Melsky et al. |
| 5,709,668 A | 1/1998 | Wacks |
| 5,713,844 A | 2/1998 | Peyman |
| 5,713,858 A | 2/1998 | Heruth et al. |
| 5,713,859 A | 2/1998 | Finch et al. |
| 5,718,382 A | 2/1998 | Jaeger |
| 5,718,682 A | 2/1998 | Tucker |
| 5,725,507 A | 3/1998 | Petrick |
| 5,733,336 A | 3/1998 | Neuenfeldt et al. |
| 5,733,400 A | 3/1998 | Gore et al. |
| 5,741,128 A | 4/1998 | Lambrecht et al. |
| 5,743,873 A | 4/1998 | Cai et al. |
| 5,743,891 A | 4/1998 | Tolkoff et al. |
| 5,746,460 A | 5/1998 | Marohl et al. |
| 5,758,667 A | 6/1998 | Slettenmark |
| 5,769,823 A | 6/1998 | Otto |
| 5,773,552 A | 6/1998 | Hutchings et al. |
| 5,776,188 A | 7/1998 | Shepherd et al. |
| 5,792,104 A | 8/1998 | Speckman et al. |
| 5,792,116 A | 8/1998 | Berg et al. |
| 5,810,789 A | 9/1998 | Powers et al. |
| 5,824,071 A | 10/1998 | Nelson et al. |
| 5,830,172 A | 11/1998 | Leveen et al. |
| 5,833,654 A | 11/1998 | Powers et al. |
| 5,835,563 A | 11/1998 | Navab et al. |
| 5,836,935 A | 11/1998 | Ashton et al. |
| 5,840,063 A | 11/1998 | Flaherty |
| 5,843,069 A | 12/1998 | Butler et al. |
| 5,853,394 A | 12/1998 | Tolkoff et al. |
| 5,868,702 A | 2/1999 | Stevens et al. |
| 5,882,353 A | 3/1999 | Vanbeek et al. |
| 5,895,424 A | 4/1999 | Steele et al. |
| 5,906,596 A | 5/1999 | Tallarida |
| 5,908,414 A | 6/1999 | Otto et al. |
| 5,913,998 A | 6/1999 | Butler et al. |
| 5,916,263 A | 6/1999 | Goicoechea et al. |
| 5,919,160 A | 7/1999 | Sanfilippo |
| 5,925,017 A | 7/1999 | Kriesel et al. |
| 5,925,030 A | 7/1999 | Gross et al. |
| 5,928,197 A | 7/1999 | Niehoff |
| 5,931,829 A | 8/1999 | Burbank et al. |
| 5,935,084 A | 8/1999 | Southworth |
| 5,944,023 A | 8/1999 | Johnson et al. |
| 5,944,688 A | 8/1999 | Lois |
| 5,944,712 A | 8/1999 | Frassica et al. |
| 5,947,953 A | 9/1999 | Ash et al. |
| 5,951,512 A | 9/1999 | Dalton |
| 5,951,522 A | 9/1999 | Rosato et al. |
| 5,954,687 A | 9/1999 | Baudino |
| 5,957,890 A | 9/1999 | Mann et al. |
| 5,968,011 A | 10/1999 | Larsen et al. |
| 5,970,162 A | 10/1999 | Kawashima |
| 5,989,216 A | 11/1999 | Johnson et al. |
| 5,989,239 A | 11/1999 | Finch et al. |
| 5,997,524 A | 12/1999 | Burbank et al. |
| 6,007,516 A | 12/1999 | Burbank et al. |
| 6,013,051 A | 1/2000 | Nelson |
| 6,013,058 A | 1/2000 | Prosl et al. |
| 6,017,331 A | 1/2000 | Watts et al. |
| 6,022,335 A | 2/2000 | Ramadan |
| 6,033,389 A | 3/2000 | Cornish |
| 6,039,712 A | 3/2000 | Fogarty et al. |
| 6,077,756 A | 6/2000 | Lin et al. |
| 6,086,555 A | 7/2000 | Eliasen et al. |
| 6,090,066 A | 7/2000 | Schnell |
| 6,102,884 A | 8/2000 | Squitieri |
| 6,113,572 A | 9/2000 | Gailey et al. |
| 6,120,492 A | 9/2000 | Finch et al. |
| 6,161,033 A | 12/2000 | Kuhn |
| 6,171,198 B1 | 1/2001 | Lizama et al. |
| 6,171,298 B1 | 1/2001 | Matsuura et al. |
| 6,174,330 B1 | 1/2001 | Stenson |
| 6,190,352 B1 | 2/2001 | Haarala et al. |
| 6,193,684 B1 | 2/2001 | Burbank et al. |
| 6,198,807 B1 | 3/2001 | Desena |
| 6,203,570 B1 | 3/2001 | Baeke |
| 6,213,973 B1 | 4/2001 | Eliasen et al. |
| 6,228,088 B1 | 5/2001 | Miller et al. |
| 6,251,059 B1 | 6/2001 | Apple et al. |
| D445,175 S | 7/2001 | Tertheas |
| 6,269,148 B1 | 7/2001 | Jessop et al. |
| 6,287,293 B1 | 9/2001 | Jones et al. |
| 6,290,677 B1 | 9/2001 | Arai et al. |

(56) References Cited

U.S. PATENT DOCUMENTS

| | | | |
|---|---|---|---|
| 6,302,875 B1 | 10/2001 | Makower et al. |
| 6,305,413 B1 | 10/2001 | Fischer et al. |
| D450,115 S | 11/2001 | Bertheas |
| 6,332,874 B1 | 12/2001 | Eliasen et al. |
| 6,347,241 B2 | 2/2002 | Burbank et al. |
| 6,355,021 B1 | 3/2002 | Nielsen et al. |
| 6,356,782 B1 | 3/2002 | Sirimanne et al. |
| 6,361,557 B1 | 3/2002 | Gittings et al. |
| 6,398,764 B1 | 6/2002 | Finch et al. |
| 6,459,772 B1 | 10/2002 | Wiedenhoefer et al. |
| 6,527,754 B1 | 3/2003 | Tallarida et al. |
| 7,713,251 B2 | 5/2010 | Tallarida et al. |
| 7,785,302 B2 | 8/2010 | Powers |
| 10,052,470 B2 | 8/2018 | Powers et al. |
| 10,179,230 B2 | 1/2019 | Powers et al. |
| 10,183,157 B2 | 1/2019 | Powers et al. |
| 10,625,065 B2 | 4/2020 | Powers et al. |
| 2001/0016717 A1 | 8/2001 | Haarala et al. |
| 2001/0051766 A1 | 12/2001 | Gazdzinski |
| 2001/0053889 A1 | 12/2001 | Marggi et al. |
| 2001/0056266 A1 | 12/2001 | Tallarida et al. |
| 2004/0157952 A1 | 8/2004 | Soffiati et al. |
| 2006/0173410 A1 | 8/2006 | Moberg et al. |
| 2006/0173424 A1 | 8/2006 | Conlon |
| 2006/0178647 A1 | 8/2006 | Stats |
| 2006/0224129 A1 | 10/2006 | Beasley et al. |
| 2007/0185462 A1 | 8/2007 | Byrum |
| 2007/0233018 A1 | 10/2007 | Bizup et al. |
| 2007/0270770 A1 | 11/2007 | Bizup |
| 2008/0319399 A1* | 12/2008 | Schweikerf | A61M 5/007 604/175 |
| 2019/0134373 A1 | 5/2019 | Barron et al. |
| 2019/0151641 A1 | 5/2019 | Powers et al. |
| 2019/0217073 A1 | 7/2019 | Maniar et al. |
| 2019/0252603 A1 | 8/2019 | Wiley et al. |
| 2019/0275311 A1 | 9/2019 | Hibdon et al. |
| 2020/0086105 A1 | 3/2020 | Powers et al. |

FOREIGN PATENT DOCUMENTS

| | | |
|---|---|---|
| DE | 19745654 A1 | 4/1999 |
| EP | 0619101 A1 | 10/1994 |
| EP | 0750520 81 | 8/2000 |
| EP | 1238682 A2 | 9/2002 |
| EP | 1896117 B1 | 1/2011 |
| FR | 2569987 A1 | 3/1986 |
| FR | 2586569 A1 | 3/1987 |
| GB | 2203342 | 10/1988 |
| JP | 2500388 Y2 | 6/1996 |
| JP | H08168322 A | 7/1996 |
| JP | 2602109 B2 | 4/1997 |
| JP | 2003102831 A | 4/2003 |
| JP | 2004350937 A | 12/2004 |
| JP | 2006-500087 A | 1/2006 |
| JP | 2006025948 A | 2/2006 |
| WO | 8600213 A1 | 1/1986 |
| WO | 9514504 A1 | 6/1995 |
| WO | 9701370 A1 | 1/1997 |
| WO | 9706845 A1 | 2/1997 |
| WO | 9711726 A1 | 4/1997 |
| WO | 9817337 A1 | 4/1998 |
| WO | 9942166 A1 | 8/1999 |
| WO | 0033901 A1 | 6/2000 |
| WO | 0047264 A1 | 8/2000 |
| WO | 0247549 A1 | 6/2002 |
| WO | 02100480 A2 | 12/2002 |
| WO | 03037215 A2 | 5/2003 |
| WO | 03086508 A1 | 10/2003 |
| WO | 2004/004800 A2 | 1/2004 |
| WO | 2004071555 A2 | 8/2004 |
| WO | 2004091434 A2 | 10/2004 |
| WO | 2005037055 A2 | 4/2005 |
| WO | 2005075614 A1 | 8/2005 |
| WO | 2006078915 A2 | 7/2006 |
| WO | 2006096686 A1 | 9/2006 |
| WO | 2006116438 A2 | 11/2006 |
| WO | 2006130133 A1 | 12/2006 |
| WO | 2006134100 A1 | 12/2006 |
| WO | 2007079024 A2 | 7/2007 |
| WO | 2007092210 A1 | 8/2007 |
| WO | 2007094898 A2 | 8/2007 |
| WO | 2007098771 A2 | 9/2007 |
| WO | 2007109164 A2 | 9/2007 |
| WO | 2007126645 A2 | 11/2007 |
| WO | 2007136538 A2 | 11/2007 |
| WO | 2008008126 A2 | 1/2008 |
| WO | 2008019236 A1 | 2/2008 |
| WO | 2008048361 A1 | 4/2008 |
| WO | 2008063226 A2 | 5/2008 |
| WO | 2008147760 A1 | 12/2008 |
| WO | 2008157763 A1 | 12/2008 |
| WO | 2009002839 A1 | 12/2008 |

OTHER PUBLICATIONS

Guidance on Medical Device Patient Labeling; Final Guidance for Industry and FDA Reviewers, Apr. 19, 2001, 54 pages.

IsoMed Constant-Flow Infusion System (Year: 2000), 111 pages.

Reminders from FDA Regarding Ruptured Vascular Access Devices from Power Injection, Jul. 2004, 2 pages.

Signs, Symbols, and Icons: Pre-history to the Computer Age, author: Rosemary Sassoon and Albertine Gaur, first published in 1997, 1997, 3 pages.

U.S. Appl. No. 60/658,518, filed Mar. 4, 2005, 78 pages.

U.S. Appl. No. 60/675,309, filed Apr. 27, 2005, 100 pages.

Carlson et al., "Safety Considerations in the Power Injection of Contrast Media via Central Venous Catheters During Computed Tomography Examinations", Investigative Radiology, vol. 27, No. 5, May 1992, pp. 337-340.

Coyle et al., "Power Injection of Contrast Media via Peripherally Inserted Central Catheters for CT", The Journal of the Association for Vascular Access (JAVA), vol. 15, No. 8, Aug. 2004, pp. 809-814.

Herts et al., "Power Injection of Contrast Media Using Central Venous Catheters: Feasibility, Safety and Efficacy", AJR:176(2), Feb. 2001, pp. 447-453.

Herts et al., "Power Injection of Intravenous Contrast Material Through Central Venous Catheters for CT: In Vitro Evaluation", Radiology, vol. 200, No. 3, Sep. 1996, pp. 731-735.

Salis et al., "Maximal Flow Rates Possible during Power Injection through Currently Available PICCs: An In-Vitro Study", Journal of the Association for Vascular Access, vol. 15, No. 3, Mar. 2004, pp. 275-281.

Sawyer, "Do It by Design: An Introduction to Human Factors in Medical Devices", U.S. Department of Health and Human Services, Public Health Service, Food and Drug Administration, Center for Devices and Radiological Health, Dec. 1996, 55 pages.

Stevens et al., "A Randomized, Prospective Trial of Conventional Vascular Ports vs. The Vortex "Clear-Flow" Reservoir Port in Adult Oncology Patients", The Journal of Vascular Access Devices, 2000, pp. 37-40.

9.75/1 0.0 em LAP-BAND System vs. 11 em LAP-BAND System: For Product Manufactured Prior to Jul. 2001, LAP-BAND System Access Port Fill Guide I BioEnterics Corporation, Jul. 1, 2001, 1 page.

BARD Access System product drawings representative of the BARD Access System products on the market on or around Mar. 1995, as indicated by the BARD Access Systems 1995 Product Release to Market form for "M.R.I. Port with8 Fr. ChronoFiex Catheter," "M.R.I. Port with 8 Fr. ChronoFiex Catheter with Intro-EzeTM,", "M.R.I. Port with 8 Fr. Chrono-Flex Catheter and Peel Apart," "M.R.I. Port with 8 Fr. ChronoFiex Catheter Demo Kit,", Mar. 21, 1995, 6 pages.

Declaration of Kelly Christian, Director of Product Development at BARD Access Systems, Inc, in support of and depicting a product on the market by Quinton Company approximately ten years prior to Oct. 22, 2009, Oct. 22, 2009, 1 page.

Extravasation of Radiologic Contrast, PA-PSRS Patient Safety Advisory, vol. 1, No. 3,, Sep. 2004, 6 pages.

(56) References Cited

OTHER PUBLICATIONS

Extreme Access, Bard Access Systems, Inc., Product Brochure, 2003, 5 pages.
Steinbach et al., "Breast Implants, Common Complications, and Concurrent Breast Disease", RadioGraphies,vol. 13, No. 1, 1993, pp. 95-118.
Shah Tilak M., "Radiopaque Polymer Formulations for Medical Devices", Medical Device and Diagnostic Industry, Mar. 2000, 6 pages.
Product Specifications, Port-A-Cath P.A.S. Port Systems by Deltec, 1999, 2 pages.
Smith Lisa Hartkoph, "Implanted Ports, Computer Tomography, Power Injectors, and Catheter Rupture", Clinical Journal of Oncology Nursing, vol. 12, No. 5, Oct. 2008, 4 pages.
Smiths Medical MD, INC.,"510(k) Premarket Notification for PORT-A-GATH and Port-A-Gath II Power PAC. Implantable Venous Access Systems and Gripper Plus Power PAC. Needle", May 23, 2007, 9 pages.
User Manual for the ESPrit 3G Apeech Processor and Accessories, Nucleus Cochlear Implant Systems; available at <http://www.cochlearamericas.com/PDFs/UserManuaiSprint.pdf>, Issue 2, Dec. 2001, 2 pages.
Biffi et al., "A Randomized, Prospective Trial of Central Venous Ports Connected to Standard Open-Ended or Groshong Catheters in Adult Oncology Patients", American Cancer Society vol. 92,No. 5, Sep. 1, 2001, pp. 1204-1212.
Biffi, et al., "Best Choice of Central Venous Insertion Site for the Prevention of Catheter-Related Complications in Adult Patients Who Need Cancer Therapy: A Randomized Trial.", Annals of Oncology, Jan. 29, 2009, 6 pages.
Biffi, et al., "Use of totally implantable central venous access ports for high-dose chemotherapy and peripheral blood stem cell transplantation: results of a monocentre series of 376 patients.", Annals of Oncology vol. 15, 2004, 5 pages.
Bioenterics® Lap-Band®,"Adjustable Gastric Banding System", by Inamed Health, Product Brochure,, Dec. 1, 2003, 22 pages.
Solomon et al., "CIN Strategies: Anticipate, Manage, Prevent", Supplement to imaging Economics, May 2007, 20 Pages.
Costa et al., "Understanding Contrast Media", Journal of Infusion Nursing, vol. 27, No. 5, Sep./Oct. 2004, 11 pages.
Costa, Nancy, "More Than Skin Deep: An Overview of Iodinated Contrast Media", Journal for the Association for Vascular Access, vol. 8, No. 4, 2003, 6 pages.
Fallscheer et al., "Injury to the Upper Extremity Caused by Extravasation of Contrast Medium Medium: A", Scandinavian Journal of Plastic and Reconstructive Surgery and Hand Surgery,vol. 41, 2007, pp. 26-32.
Sullivan et al., "Radiopaque Markers on Mammary Implants", American Journal of Roentgenology 153(2):428,, Aug. 1989, 2 pages.
Teichgraber et al., "Central Venous Access Catheters: Radiological Management of Complications", Cardiovascular and Interventional Radiology, Review Article, Jul. 31, 2003, 13 pages.
Hou, et al., "Comparisons of Outcomes and Survivals for Two Central Venous Access Port Systems", Journal of Surgical Oncology, vol. 91, 2005, 6 pages.
Johnson Kathleena, , "Power Injectable Portal Systems", Journal of Radiology Nursing, vol. 28,Issue 1, Mar. 2009, 6 pages.

Lamaitre Vascular,"Port Implantations: using the OptiLock Implantable Port", product information, available at <http://www.lemaitre.com/specs_pop.asp>, Apr. 2003, 14 pages.
Lap-Band APTM,"System with Adjustable Gastric Banding system with OMNIFORM Design", Product Brochure, Jul. 2007, 16 pages.
Lap-Band®,"Adjustable Gastric Banding System", BioEnterics Corporation, Product Brochure, 12 pages.
Lap-Band®,"System Fact Sheet, © 2007 Allergan, Inc.,", 2 pages.
Medcomp,"510(k) Summary for Power Injectable Implantable Infusion Port", May 15, 2007, 6 pages.
Medcomp,"PortCT Technology", display at SIR Conference, Toronto, Canada, Mar. 2006, 1 page.
Medtronic, Inc.,"Iso-Med Constant-Flow Infusion System", Sep. 2000, 111 pages.
Plinski et al., "Implantable Cardioverter-Defribillators: Implications for the Nonelectrophysiologist", Annals of Internal Medicine, Abstract of vol. 122 No. 10, pp. 770-777.
PORT-A-CATH®,"Many Port-A-CATH® System Choices.", Product Brochure, SIMS Deltec, Inc.,1996, 5 pages.
PORT-A-CATH®,"Single-lumen Implantable Vascular Access Systems", Product Specifications, Smith Medical, 2004, 4 pages.
PORT-A-CATH®,"Implantable Epidural, Aterial and Peritoniai Access Systems", Internet Product Listing of Nov. 19, 2000, available at <http://web. archive.org/web/20001119035900/www.deltec.com/cPacspl.htm,>, Oct. 17, 2009, 2 pages.
Rappolt et al., "Radiopaque Codification and X-ray identification of Ingested Drugs", Ingestive Radiology, May-Jun. 1966, 4 pages.
Thistlethwaite et al., "Generalized Feature-Based RSA of Orthopaedic Implants", Summer Bioengineering Conference Sonesta Beach Resort in Key Biscayne, Florida, 2 pages.
Sandstede, Joern, "Pediatric CT", <www.multislice- ct.com, MultiSLICE-CT.com>, version 02, May 2, 2003, 36 pages.
Sanelli et al., "Safety and Feasibility of Using a Central Venous Catheter for Rapid Contrast Injection Rates", American Journal of Radiology, vol. 183, Dec. 2004, pp. 1829-1834.
Sawyer Dick, "Do It by Design: An Introduction to Human Factors in Medical Devices", U.S. Department of Health and Human Services, Public Health Service, Food and Drug Administration, Center for Devices and Radiological Health, Dec. 1996, 55 pages.
U.S. Food and Drug Administratio,"Guidance for Institutional Review Boards and Clinical investigators 1998 Update: Medical Devices", Sep. 10, 2008, 13 pages.
Urquiola et al., "Using Lead Foil as a Radiopaque Marker for Computerized Tomography Imaging When Implant Treatment Planning", The Journal of Prosthetic Dentistry, vol. 77, No. 2,, Frb. 1, 1997 00:00:00.0, pp. 227-228.
Vergara et al., "Adverse Reactions to Contrast Media in CT: Effects of Temperature and Ionic Property", Radiology, vol. 199, No. 2, May 1996, 4 pages.
Vogelzang Robertl. , "Power Injection Through Central Venous Catheters: Physiological and Hemodynamic Considerations", The McGaw Medical Center of Northwestern University, Feinberg School of Medicine, 3 pages.
Wells S, "Venous Access in Oncology and Haematology Patients: Part One", Nursing Standard, vol. 22, No. 52, pp. 39-46,, Sep. 3, 2008, 9 pages.
Williamson et al., "Assessing the Adequacy of Peripherally Inserted Central Catheters for Power Injection of Intravenous Contrast Agents for CT", Journal of Computer Assisted Tomography, vol. 6, No. 6, 2001, pp. 932-937.

\* cited by examiner

VENOUS ACCESS PORT ASSEMBLY WITH X-RAY DISCERNABLE INDICIA

CROSS-REFERENCE TO RELATED APPLICATION

This application is a continuation application of Ser. No. 15/441,762, filed Feb. 24, 2017, which is a continuation application of, and claims the benefit of, co-pending U.S. patent application Ser. No. 12/175,270, filed Jul. 17, 2008, now U.S. Pat. No. 9,610,432, issued Apr. 4, 2017, which claims the benefit of U.S. Provisional Patent Application Ser. No. 60/961,160, filed Jul. 19, 2007, the disclosures of which are incorporated by reference in their entirety.

FIELD OF THE INVENTION

This relates to the field of medical devices and more particularly to venous access ports for the infusion of fluids into the patient and/or withdrawal of fluids from the patient.

BACKGROUND OF THE INVENTION

Venous access ports for the infusion and/or withdrawal of fluids from a patient are well-known, secured to the proximal end of an implanted catheter. These ports are typically used for drug infusion or for withdrawal of small amounts of blood, where large flows of fluid are not required. The ports are assemblies of a needle-impenetrable housing with a discharge port in fluid communication with the catheter and the reservoir within the port housing, and provide a subcutaneous self-sealing septum that defines an access site for multiple needle sticks through the covering skin tissue of the patient, through the septum and into the reservoir, without the need to continuously search for new access sites. Examples of such ports are disclosed, for example, in U.S. Pat. Nos. 4,704,103; 4,762,517; 4,778,452; 5,185,003; 5,213,574; 5,637,102; and 5,833,654. In U.S. Pat. No. 5,833,654 is set forth a dual chamber port assembly having a metal casing as a liner in one of the chambers of the port assembly.

It is desired to provide a venous access port assembly that provides for a radiologist, radiology technologist, nurse and ultimately a medical practitioner to be able to discern an important property of the port assembly after the port assembly has been implanted into a patient.

BRIEF SUMMARY OF THE INVENTION

The present invention is related to a venous access port having a housing and a septum, providing an interior reservoir and a passageway extending from the reservoir through a stem of a discharge port to establish fluid communication with a proximal end of a catheter lumen to which the port assembly is secured prior to placement of the assembly into a patient. The port may optionally have more than one reservoir and associated septum. The invention is the incorporation of X-ray discernable indicia onto a venous access port that is discernible under X-ray examination to provide information concerning the nature or key attribute of the venous access port, so that the practitioner, subsequent to the date of implantation thereof, can determine that nature or key attribute under X-ray examination. One such key attribute in particular would be, for example, that where the venous access port is rated to be used for power injection, such as used for contrast fluid injection during a contrast enhanced computed tomography, the letters "CT" (for "computed tomography) would be provided on the port assembly in such a manner that they are radiographically visible. The attribute in this example is the property of the port's being adapted to withstand high pressures that are used for injection of contrast fluid into a patient, and the letters "CT" would be understood in medical practice to indicate that the port is suitable for the high pressure injection of contrast fluid.

In the preferred embodiment, a reservoir lining of radiopaque material such as titanium, includes cutouts such as of letters "CT" (although other indicia may be utilized) through the body of the lining, with the cutouts being radiographically visible. The lining for the reservoir is contained within the port housing and includes an aperture through the side wall for fluid communication with a discharge stem of the port assembly, establishing fluid communication with a catheter sealingly and securely affixed to the discharge stem of the assembly. The reservoir lining of titanium provides protection against penetration by a needle when it is inserted through the septum of the port assembly for injection of fluid into the chamber. The letters "CT" are readable from exterior of the patient in an X-ray. The lining may have several such sets of cutouts located at various locations about the lining's side wall and/or in the bottom wall thereof. The cutouts preferably are substantially narrow for exposing therethrough only a minimum amount of plastic of the surrounding housing.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION OF THE INVENTION

Figure 1:
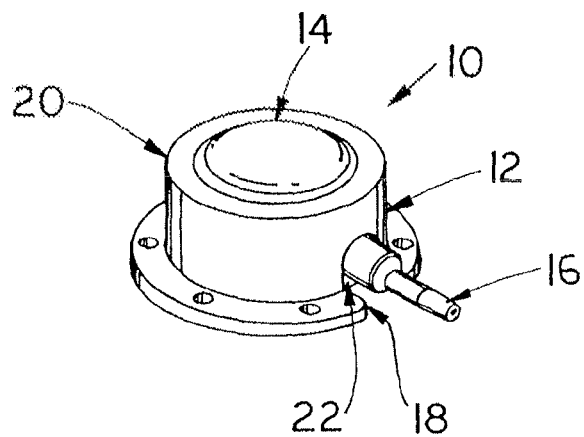
FIGS. 1 and 2 are an isometric view and an exploded view, respectively, of the venous access port assembly containing the present invention.

Certain terminology is used herein for convenience only and is not to be taken as a limitation on the present invention. The terms "distal" and "proximal" refer, respectively, to directions closer to and away from the insertion tip of a catheter in an implantable catheter assembly. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Venous access port assembly 10 of FIGS. 1, 2, 5 and 6 includes a housing 12 and a septum 14, with a discharge stem 16 extending from a distal end 18 of the port assembly 10 to be attached securely and sealingly to the proximal end of a catheter (not shown). Cap 20 of housing 12 secures to housing base 22 to in turn secure septum 14 in position in the port assembly 10 in a manner that exposes the top surface of the septum for needle insertion. A passageway 24 (see FIGS. 5 and 6) extends from an interior reservoir 26 to the distal tip opening 28 of discharge stem 16. A recess 30 is seen to be provided along both sides of discharge stem 16, facilitating insertion of the discharge stem 16 into the catheter lumen and providing a clearance for a locking sleeve or clamp (not shown) utilized to compress the catheter lumen wall against the exterior surface of the discharge port 16 for assured sealed connection of the catheter with the port assembly 10.

Figure 2:
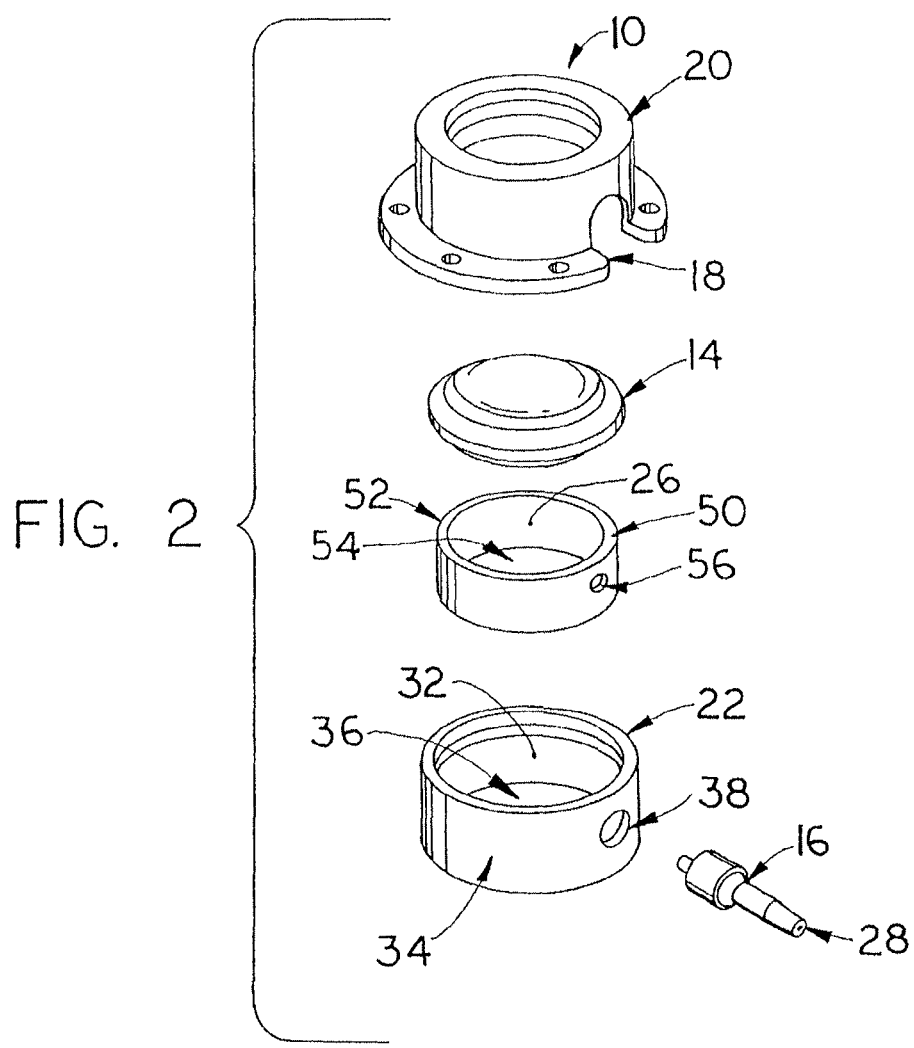
Figure 3:
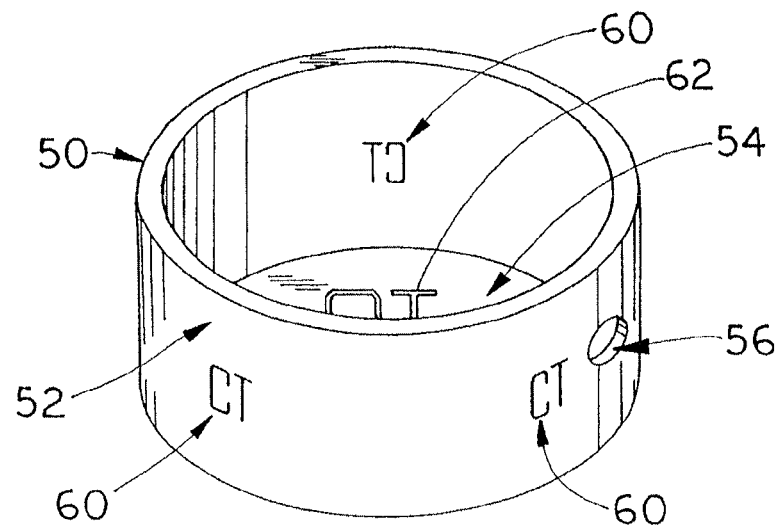
FIG. 3 is an isometric view of a reservoir lining of the present invention defining X-ray discernable indicia.
Figure 4:
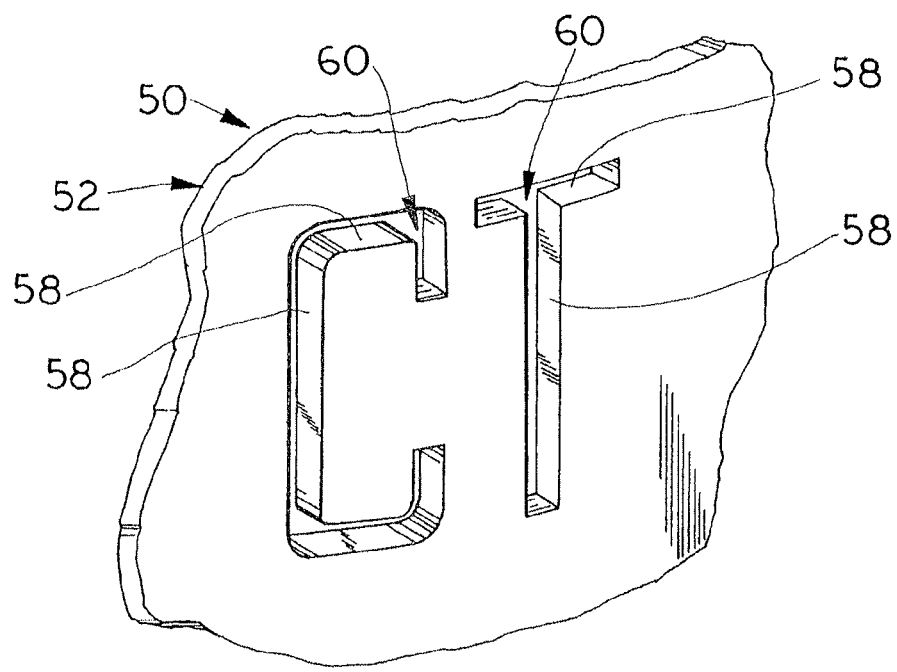
FIG. 4 is an enlarged view of portion of the lining of FIG. 3 illustrating the cutout indicia provided by the lining.
Figure 5:
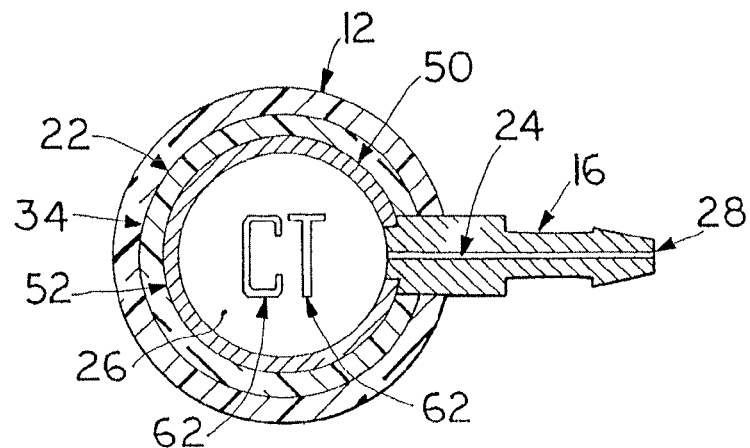
FIGS. 5 and 6 are cross-section views of the port of FIGS. 1 and 2.
Figure 6:
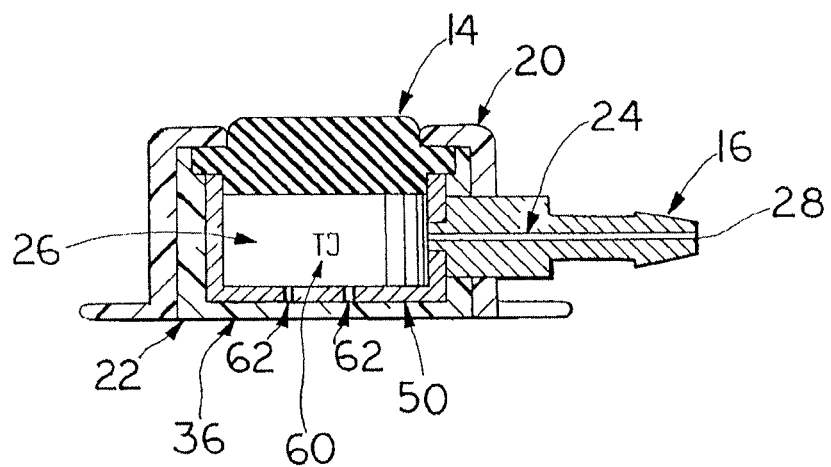

With reference now to FIGS. 2 to 4, showing reservoir lining 50 of the present invention, lining 50 is cup-shaped and is inserted into well 32 of housing base 22 beneath septum 14, and secured therewithin. Lining 50 is made of needle-impenetrable material such as metal, which may be titanium or stainless steel, and its side wall 52 and bottom wall 54 protects the side walls 34 and bottom wall 36 of housing base 22 defining well 32, from being penetrated by a needle (not shown) inserted into and through septum 14 for injection of fluids into reservoir 26 or withdrawal of blood therefrom. An aperture 56 near or at the bottom of side wall 52, in alignment with a corresponding aperture 38 of housing base 22, establishes fluid communication with passageway 24 of discharge stem 16 for fluid to pass between the reservoir 26 and the catheter and thus the patient. Discharge stem 16 may be a metal component such as titanium or stainless steel which would extend through aperture 38 of the housing base 22, to preferably be welded to lining 50.

In accordance with the present invention, the X-ray discernable indicia are cutouts 60 formed through the body of lining 50, shown as the alphabetical letters "CT". The letters "CT" are visible when the X-ray of the patient is viewed, readable from outside the lining 50 and are easily discerned by the radiologist or technologist. In lining 50, preferably a plurality of sets of cutout indicia 60, 62 are provided equi-angularly spaced about the circumference of the side wall 52 and through bottom wall 54 to assure that the indicia appear in the X-ray irrespective of the angular location at which the X-ray is taken. With particular reference to FIG. 4, it is preferable that the width of each cutout slot 58 of the indicia or letters be as narrow as possible but still be discernable by X-ray; the narrowness of the slots 58 minimizes any possibility that a needle inserted through the septum could penetrate through a slot of a cutout by chance, thus harming the patient and resulting in injection of fluid directly into the tissue surrounding the port. The width of each cutout slot 58 would thus preferably be less wide than the diameter of a needle. The set of cutout indicia 62 through the bottom wall may be dimensionally larger as a set, but still with narrow slot width. Centering of the cutout indicia 62 along the bottom wall 54 positions the indicia directly beneath the reservoir and septum, minimizes any obscuring thereof by the structure of the venous access port assembly, and the indicia may also be easily discernable should the port assembly be at an angle from the horizontal plane of the X-ray.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A venous access port assembly for implantation into a patient, comprising:
   a housing, comprising a housing base;
   a reservoir lining defining a reservoir, wherein the reservoir lining comprising a needle impenetrable radiopaque material;
   a discharge port extending from the housing, the discharge port comprising a discharge stem forming a fluid passageway between the reservoir and the discharge port; and
   an X-ray discernable indicium that indicates an attribute of the venous access port assembly when X-rays are incident upon the venous access port assembly, wherein the X-ray discernable indicium is cut in at least a part of the reservoir lining.

2. The assembly of claim 1, wherein the reservoir lining is cup-shaped with an open end.

3. The assembly of claim 1, wherein the radiopaque material is metal.

4. The assembly of claim 1, wherein the radiopaque material is titanium.

5. The assembly of claim 1, wherein the X-ray discernable indicium comprises at least one alphabetical letter.

6. The assembly of claim 2, wherein the X-ray discernable indicium comprises a plurality of cuts in a side wall of the reservoir lining.

7. The assembly of claim 2, wherein the X-ray discernable indicium comprises at least one cut in a bottom wall of the reservoir lining.

8. The assembly of claim 2, wherein the X-ray discernable indicium comprises a plurality of cuts in a side wall and a bottom wall of the reservoir lining.

9. The assembly of claim 2, wherein the at least one cut is formed as at least one narrow slot having a width only sufficiently wide to be X-ray discernable.

10. The assembly of claim 2, wherein the X-ray discernable indicium is centered in a bottom wall of the reservoir lining.

* * * * *